United States Patent [19]

Hickel et al.

[11] Patent Number: 5,028,132

[45] Date of Patent: Jul. 2, 1991

[54] EXAMINATION OF SURFACE STRUCTURE

[75] Inventors: Werner Hickel, Mannheim; Wolfgang Knoll, Mainz; Benno Rothenhaeusler, Burgberg, all of Fed. Rep. of Germany

[73] Assignee: BASF Aktiengesellschaft, Ludwigshafen, Fed. Rep. of Germany

[21] Appl. No.: 494,403

[22] Filed: Mar. 16, 1990

[30] Foreign Application Priority Data

Mar. 21, 1989 [DE] Fed. Rep. of Germany ....... 3909143

[51] Int. Cl.$^5$ ............................................ G01B 11/00
[52] U.S. Cl. .................. 356/256; 356/318; 356/372; 356/376; 356/445
[58] Field of Search .............. 356/128, 372, 375, 376, 356/237, 317, 318, 445, 418, 256

[56] References Cited

PUBLICATIONS

Surface Polaritions–Propagating Electromagnetic ..., Burstein et al., J. Vac. Sci. Technol., vol. 11, No. 6, Nov./Dec. 1974, 1004–1019.
Physics of Thin Film, Raether, Academic Press, pp. 145–259.
Photoacoustic Observation of Nonradiative Decay ..., Inagaki et al., Physical Review B, vol. 24, No. 6, Sep. 1981.
On the Decay of Plasmon Surface Polaritons at Smooth ..., Rothenhausler et al., Surface Science 137 (1984), 373–383.
On the Influence of the Propagation Length of Plasmon ..., Surface Science 191 (1987), 585–594.
Oberflächenwellen und Brewster fall, ..., Otto, OPTIK 38 (1973).
Propagation of Surface Polaritons Over Macroscopic ... Solid State Comm., vol. 12, pp. 185–189, 1973, Pergamon Press, Schoenwald et al.

Primary Examiner—F. L. Evans
Attorney, Agent, or Firm—Keil & Weinkauf

[57] ABSTRACT

A technique for examining surface structures which differ in respect of refractive index and/or height modulation of the surface comprises introducing these surface structures into a plasmon surface polariton field and scanning them by means of surface plasmon microscopy.

4 Claims, 2 Drawing Sheets

EXAMINATION OF SURFACE STRUCTURE

The present invention relates to a technique for examining surface structures in respect of refractive index and/or height modulation of the surface.

Plasmon surface polaritons (PSPs) are bound, nonradiative electromagnetic modes which travel along a metal/dielectric interface (cf. E. Burstein, W.P. Chen and A. Hartstein, J. Vac. Sci. Technology 11 (1974), 1004, and H. Raether in: Physics of Thin Films (eds. G. Hass, M.H. Francombe and R.W. Hoffmann), vol. 9, 145-261 (Academic Press, NY, 1977). Their field intensity, which is at a maximum at the metal surface, decays exponentially perpendicular to the surface, not only into the metal but also into the dielectric (ie. bound waves), but as a consequence of dissipative (cf. T. Inagaki, K. Kagami and E.T. Arakawa, Phys. Rev. B24 (1981), 3644; B. Rothenhäusler, J. Rabe, Korpiun and W. Knoll, Surf.Sci. 137 (1984), 373, and B. Rothenhäusler and W. Knoll, Surf.Sci. 191 (1987), 585) and radiative losses is also damped in the propagation direction (cf. A. Otto, Optik 38 (1973), 566 and J. Schoenwald, E. Burstein and J.M. Elson, Solid State Commun. 12 (1973), 185).

The PSP-based technique of surface plasmon microscopy (SPM) as hitherto practiced requires that the thin film to be examined be applied to a metal or semiconductor film. In addition, this technique is only suitable for examining thin films $\leq 1$ $\mu$m.

To this end PSPs are excited with a coupling arrangement (for example a grating or prism). Preference is given to the Kretschmann configuration, where monochromatic parallel light, preferably from a helium-neon laser or an argon ion laser, is incident at an angle $\Theta$ on a prism whose base has been coated with a thin metal or semiconductor film. The metal film is preferably made of silver, gold or a layer assembly of chromium and gold. If this metal film is coated with a structured thin film, the latter can be visualized by SPM using PSP light. This technique permits a very high vertical resolution. Thickness differences of a few 0.1 nm can be visualized in this way. The disadvantage of this technique is that only thin films atop a metal can be studied.

BRIEF SUMMARY OF THE INVENTION

It is an object of the present invention to develop an SPM technique for imaging free surfaces having a height modulation and/or a structuring refractive index.

We have found that this object is achieved by a technique for examining surface structures which differ in respect of refractive index and/or height modulation of the surface, which comprises introducing these surface structures into a PSP field and scanning them by SPM.

To put the technique into effect, the surface structure can be moved by a device toward a metal or semiconductor film on a surface of a glass prism while held in an altitude parallel to said metal or semiconductor film and there is a vacuum or a transparent medium, which may be liquid or gaseous, between the surface structure to be examined and the metal or semiconductor film.

DETAILED DESCRIPTION OF THE INVENTION

The technique according to the present invention makes use of the abovementioned Kretschmann configuration not only to excite the PSPs but also for the SPM. The angle of incidence $\Theta$ of the laser is set to the PSP resonance angle, ie. the angle at which optimum coupling occurs between the PSPs and the incident light.

Figure 1:
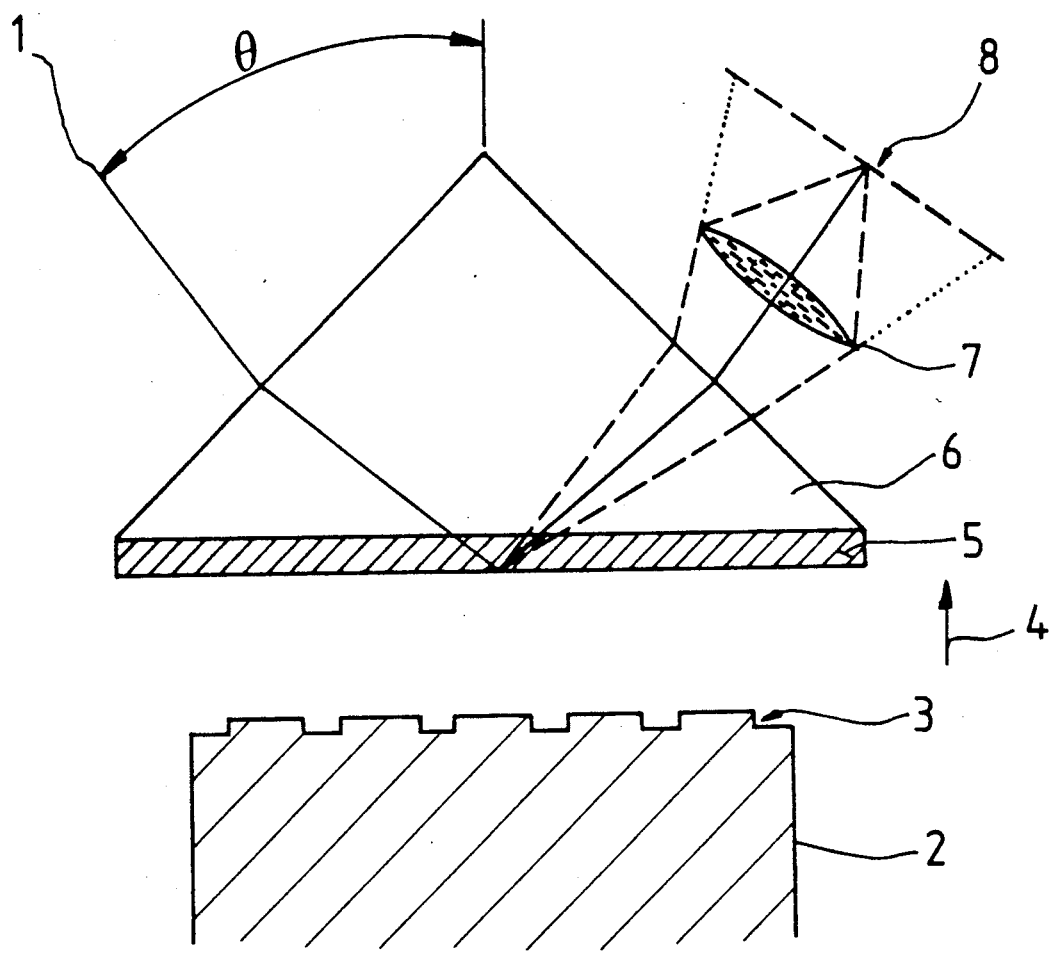
FIG. 1 shows a schematical set-up of the equipment used in the process of this invention.

The surface to be examined is then moved by a device toward the metal or semiconductor film, which is situated on one surface of the prism, while held in an attitude parallel to said metal or semiconductor film. A suitable experimental set-up is shown schematically in FIG. 1, where 1 signifies a light source (laser beam), 2 an external sample, 3 the surface structure of the external sample, 4 a lifting device, 5 a metal film (Ag), 6 a glass prism, 7 a lens, and 8 a video camera/monitor. Given a suitable distance between the surface of the sample to be examined and the metal or semiconductor film, the height or refractive index structures of the surface of said sample will disturb the PSPs of the undisturbed metal/dielectric interface to different extents, producing contrasts for visualization by SPM. SPM thus supplies an image of the surface structure of the sample. The attainable resolution is similar to that obtainable with SPM in its previously described form.

If the vacuum or gas between the metal film and the sample is replaced by a suitable immersion fluid, the SPM contrast increases.

The technique according to the present invention has the significant advantage of making it possible to examine free-surface samples moved from the outside close to the metal film on the prism.

It is possible in this way to examine surfaces of samples of different compositions, for example glass, resin, polymer, eg. films, semiconductors, eg. silicon, metals and biological substrates.

The invention is illustrated by the following Example:

EXAMPLE

Figure 2:
FIG. 2 depicts a micrograph produced by the process of the invention.

A dianegative whose surface is deeper in the exposed areas than in the unexposed areas is moved by a suitable device, comprising for example a step motor for coarse adjustment and a piezo element for fine adjustment, toward an Ag metal film on a glass prism. At a distance <200 nm, the height-modulated surface becomes visible. The micrograph depicted in FIG. 2 was recorded with an SPM set-up (see FIG. 1) at an Ag film/dianegative distance of about 10 nm. The height modulation of this sample was 0.6 $\mu$m.

We claim:

1. A process for examining surface structures which differ in respect of refractive index and/or height modulation of the surface, which comprises introducing these surface structures into a plasmon surface polariton field and scanning them by surface plasmon microscopy.

2. A process as claimed in claim 1, wherein the surface structures are moved by a device toward a metal or semiconductor film on a surface of a glass prism in an attitude parallel to said metal or semiconductor film.

3. A process as claimed in claim 2, wherein there is a vacuum or a transparent medium between the surface structure to be examined and the metal or semiconductor film.

4. A process as claimed in claim 3, wherein the transparent medium situated between the surface structures to be examined and the metal or semiconductor film is liquid or gaseous.

* * * * *